(12) United States Patent
Carter (10) Patent No.: US 12,206,653 B2
(45) Date of Patent: Jan. 21, 2025

(54) DATA EXCHANGE WITH RESOURCE CONSTRAINED TECHNOLOGY IN SURGICAL ENVIRONMENT

(71) Applicant: Proximie Inc., Boston, MA (US)

(72) Inventor: Christopher R. Carter, Haywards Heath (GB)

(*) Notice: Subject to any disclaimer, the term of this patent is extended or adjusted under 35 U.S.C. 154(b) by 235 days.

(21) Appl. No.: 18/098,147

(22) Filed: Jan. 18, 2023

(65) Prior Publication Data
US 2023/0231834 A1 Jul. 20, 2023

Related U.S. Application Data

(60) Provisional application No. 63/300,525, filed on Jan. 18, 2022.

(51) Int. Cl.
*H04L 9/40* (2022.01)
*G16H 80/00* (2018.01)
(Continued)

(52) U.S. Cl.
CPC ......... *H04L 63/0442* (2013.01); *G16H 80/00* (2018.01); *G06K 7/1417* (2013.01); *G06K 19/06112* (2013.01)

(58) Field of Classification Search
CPC .................. H04L 63/0442; H04L 63/0823
(Continued)

(56) References Cited

U.S. PATENT DOCUMENTS 10,764,752 B1 * 9/2020 Avetisov ............. H04L 63/0823
11,113,665 B1 * 9/2021 Rose .................. G06Q 20/4014
(Continued)

FOREIGN PATENT DOCUMENTS

WO 2013022780 A1 2/2013

OTHER PUBLICATIONS

International Search Report and Written Opinion in PCT/US23/10897 mailed on Jun. 27, 2023.
(Continued)

*Primary Examiner* — Teshome Hailu
(74) *Attorney, Agent, or Firm* — Schmeiser, Olsen & Watts LLP; Timothy P. Collins (57) ABSTRACT

A system and method for performing a secure data transfer between computing devices comprise registering a resource-constrained computing device with a cloud-based computer. A client computing device generates session state information regarding the client computing device in an electronic communication exchange with at least one remote computing device. An identifier provides a location of the session state information stored at a cloud-based computer. A machine-readable code associated with the identifier is displayed for querying the cloud for the stored session state information. The resource-constrained computing device uses the machine-readable code to retrieve the session state information. The resource-constrained computing device uses the session state information to join the electronic communication exchange. Alternatively, in lieu of a machine-readable code, a cryptography process is performed, which includes generating a public cryptographic certificate associated with an immutable identifier of a portable device to be integrated in the exchange.

11 Claims, 7 Drawing Sheets

(51) Int. Cl.
*G06K 7/14* (2006.01)
*G06K 19/06* (2006.01)

(58) Field of Classification Search
USPC .......................................... 713/175
See application file for complete search history.

(56) References Cited

U.S. PATENT DOCUMENTS

| | | |
|---|---|---|
| 2012/0011237 A1 | 1/2012 | Bagwandeen |
| 2014/0277595 A1 | 9/2014 | Nixon et al. |
| 2016/0087933 A1* | 3/2016 | Johnson ................. H04L 41/08 |
| | | 709/245 |
| 2017/0099293 A1* | 4/2017 | Tan ....................... H04L 67/535 |
| 2017/0235490 A1* | 8/2017 | Tan ......................... G06F 21/10 |
| | | 711/152 |
| 2018/0278612 A1* | 9/2018 | Pattar .................... H04L 63/061 |
| 2019/0261174 A1* | 8/2019 | Adler ................... H04W 12/041 |
| 2021/0266303 A1* | 8/2021 | Pollutro .............. H04L 63/0435 |
| 2022/0012795 A1 | 1/2022 | Vannoni et al. |

OTHER PUBLICATIONS

Invitation to Pay Addition Fees in PCT/US23/10897 mailed on Apr. 17, 2023.
International Preliminary Report on Patentability in PCT/US23/10897 mailed on Aug. 2, 2024.

\* cited by examiner

DATA EXCHANGE WITH RESOURCE CONSTRAINED TECHNOLOGY IN SURGICAL ENVIRONMENT

RELATED APPLICATIONS

This application claims the benefit of and priority to U.S. provisional application no. 63/300,525, filed Jan. 18, 2022, entitled "DATA EXCHANGE WITH RESOURCE CONSTRAINED TECHNOLOGY IN SURGICAL ENVIRONMENT," the entirety of which is incorporated by reference herein.

BACKGROUND

Due to modern computer technology, the medical profession has expanded to allow multiple surgeons to participate in a surgical procedure that includes computer-based collaborations with surgical staff within the operating room and/or with remote participants. In doing so, modern medical facilities such as operating rooms include videoconferencing systems comprising cameras and microphones affixed to the ceiling, walls, stationary objects such as poles, furniture, and computer equipment. However, fixed installations impose constraints that limit the effectiveness of computer-related collaborations. A fixed computing infrastructure having stationary cameras cannot reproduce what the surgeon sees with his or her own eyes. A portable infrastructure, e.g., a having a videoconferencing camera on a laptop computer or a mobile trolley may be implemented so that some or all of the infrastructure may be moved and removed from a surgical environment. However, a portable infrastructure is difficult to implement and cannot be easily incorporated in a secure manner into a fixed medical facility. Also, the participation of an external computing environment in a videoconferencing session with remote participants can expose the video and audio feeds exchanged outside the operating room to security issues, such as malicious software (malware) attacks, and so on.

SUMMARY

In brief overview, provided are a system and method that address the foregoing disadvantages of a fixed videoconferencing infrastructure in an operating room and overcomes the conventional problems of implementing a portable infrastructure. Some embodiments of the present inventive concept include a system that seamlessly integrates a fixed videoconferencing infrastructure with a resource-constrained device, for example, a computing device worn on the body, referred to as a wearable computing device or wearable device, although other resource-constrained electronic devices may equally apply. The wearable device may participate in a videoconferencing session quickly and securely with minimal interaction by pointing a camera or other scanning device of the wearable device at an ephemeral identification source such as a barcode, e.g., a quick response (QR) code) or a human readable sequence of digits that uniquely permit the wearable device to electronically communicate with, i.e., pair with, a fixed videoconferencing infrastructure to securely access a videoconferencing session (which may include an exchange of video, audio, and/or data) that includes the fixed videoconferencing infrastructure. In this embodiment, an authorizing device that is itself appropriately authorized to authorize other devices securely communicates the means of authentication to the intended new participating device. In one example, referring to FIG. 1, an authorizing device may be a fixed, immobile or large monolithic videoconferencing system, which operates as an authorizing device to authorize a wearable device. However, in another example, the authorizing device can be any device that the user has already logged into that is connected to the fixed infrastructure, such as the abovementioned immobile videoconferencing system, or a portable device, for example, described in some embodiments herein. Here, either the fixed videoconferencing system or the portable device can provide an ephemeral identification source, e.g., either device 40 or 22 shown in FIG. 1, with respect to generating the identifier for one time use.

In an alternative embodiment, an authorizing device obtains the identity of the intended participating device by reading an immutable permanent identifier of the intended participating device such as a quick response (QR) code, near-field communication (NFC) tag, or radio frequency identification (RFID) chip attached to the intended participating device and uses a commonly accessible existing server infrastructure to communicate an alternative appropriate means authorization. Instead of conventional ephemeral identifiers, some embodiments herein describe the identifier being immutably associated to a device, and the authorizing device instructing a computer, server, cloud, or other intelligent electronic device to allow entry.

In one aspect, a method for performing a secure data transfer between computing devices comprises: registering a resource-constrained computing device with a cloud-based computer; generating, by a client computing device, session state information regarding the client computing device in an electronic communication exchange with at least one remote computing device; storing the session state information at the cloud-based computer; generating an identifier that provides a location of the session state information stored at the cloud-based computer; displaying a machine-readable code associated with the identifier for querying the cloud computing computer for the stored session state information; processing, by the resource-constrained computing device, the machine-readable code to retrieve the session state information from the cloud-based computer; and processing, by the resource-constrained computing device, the session state information to integrate the resource-constrained computing device with the client computing device to participate in the electronic communication exchange with the at least one remote computing device.

In another aspect, a method for performing a secure data transfer between computing devices comprises registering a portable device with a cloud-based computer, including: generating a public cryptographic certificate associated with an immutable identifier of the portable device; and generating a private key associated with the public cryptographic certificate. The method further comprises generating, by a client computing device, session credentials regarding an electronic communication exchange between the client computing device and at least one remote computing device; encrypting the session credentials using the public cryptographic certificate; storing the encrypted session credentials at the cloud-based computer; decrypting, by the portable device, the encrypted session credentials using the private key; and processing, by the portable device, the session credentials to integrate the portable device with the stationary computing device to participate in the electronic communication exchange with the client computing device and at least one remote computing device.

In another aspect, a system for secure data transfer between computing devices comprises a client computing device in a communication session with at least one remote computing device, the client computing device; and a mobile computing device, comprising: a processor; a memory coupled to the processor; and a wireless input/output device in communication with the processor and memory, the mobile computing device registered with a cloud computing device to retrieve session information about the client computing device so that the mobile computing device can join the communication session with the client computing device and the at least one remote computing device.

BRIEF DESCRIPTION OF THE SEVERAL VIEWS OF THE DRAWINGS

The above and further advantages may be better understood by referring to the following description in conjunction with the accompanying drawings, in which like numerals indicate elements and features in various figures. The drawings are not necessarily to scale, emphasis instead being placed upon illustrating the principles of the concepts. In the drawings.

DETAILED DESCRIPTION

Reference in the specification to an embodiment or example means that a particular feature, structure or characteristic described in connection with the embodiment or example is included in at least one embodiment or example of the teaching. References to a particular embodiment or example within the specification do not necessarily all refer to the same embodiment or example.

The present teaching will now be described in detail with reference to exemplary embodiments or examples thereof as shown in the accompanying drawings. While the present teaching is described in conjunction with various embodiments and examples, it is not intended that the present teaching be limited to such embodiments and examples. On the contrary, the present teaching encompasses various alternatives, modifications, and equivalents, as will be appreciated by those of skill in the art. Those of ordinary skill having access to the teaching herein will recognize additional implementations, modifications, and embodiments, as well as other fields of use, which are within the scope of the present disclosure as described herein.

The fixed infrastructure of a modern medical facility, or more specifically, an operating room or the like, generally includes equipment that offers a high quality video and audio experience at the cost of constraints of viewpoints and specialism. For example, a fixed infrastructure having a videoconferencing unit with a camera and microphone cannot accurately reproduce the surgeon's viewpoint due to its location relative to the medical practitioner. For example, a camera may capture a front view of a surgeon but fail to capture a top view of the surgeon performing a medical procedure on a patient. Some facilities may have a moveable specialized infrastructure including portable infrared cameras or the like that may more accurately track blood loss sources or other important medical procedure-related information. In this example, the infrared camera may not be used frequently enough to be incorporated into every fixed infrastructure but may be shared across multiple neighboring operating rooms each of which has a dedicated separate fixed infrastructure.

To address the inability for a fixed infrastructure to display a surgeon's view, a surgeon may wear smart glasses or other wearable computers, which have a camera, optical head-mounted display, microphone, and/or other related electronic devices to at least partially allow a view of a medical practitioner to be digitally reproduced and can extend the capabilities offered by the fixed videoconferencing infrastructure. For example, wearable computer glasses worn by a surgeon can capture the perspective of the surgeon. It is desirable for data communication interactions to occur with the wearable computing device prior to or during a surgical procedure that (1) seamlessly integrates the wearable computing device into a videoconferencing session performed by other cameras, monitors, microphones, and so on in connection with the surgical procedure, (2) minimizes the requirement to physically interact with the either the fixed infrastructure of the operating room or the wearable device itself, and (3) is highly secure such that the session credentials to join a multimedia conferencing session cannot be stolen, or reused after the completion of the session. A networked communication session, e.g., an interactive real-time or near real-time videoconferencing session, may occur in accordance with a signaling protocol such as Session Initiation Protocol (SIP). Session state information corresponding to a real-time session that includes a combination of voice, video and messaging applications in which a fixed videoconferencing infrastructure participates can be copied to the wearable device so that the wearable device can instantly access the same real-time images, data, and so on as the fixed videoconferencing infrastructure in a secure manner.

Figure 1:
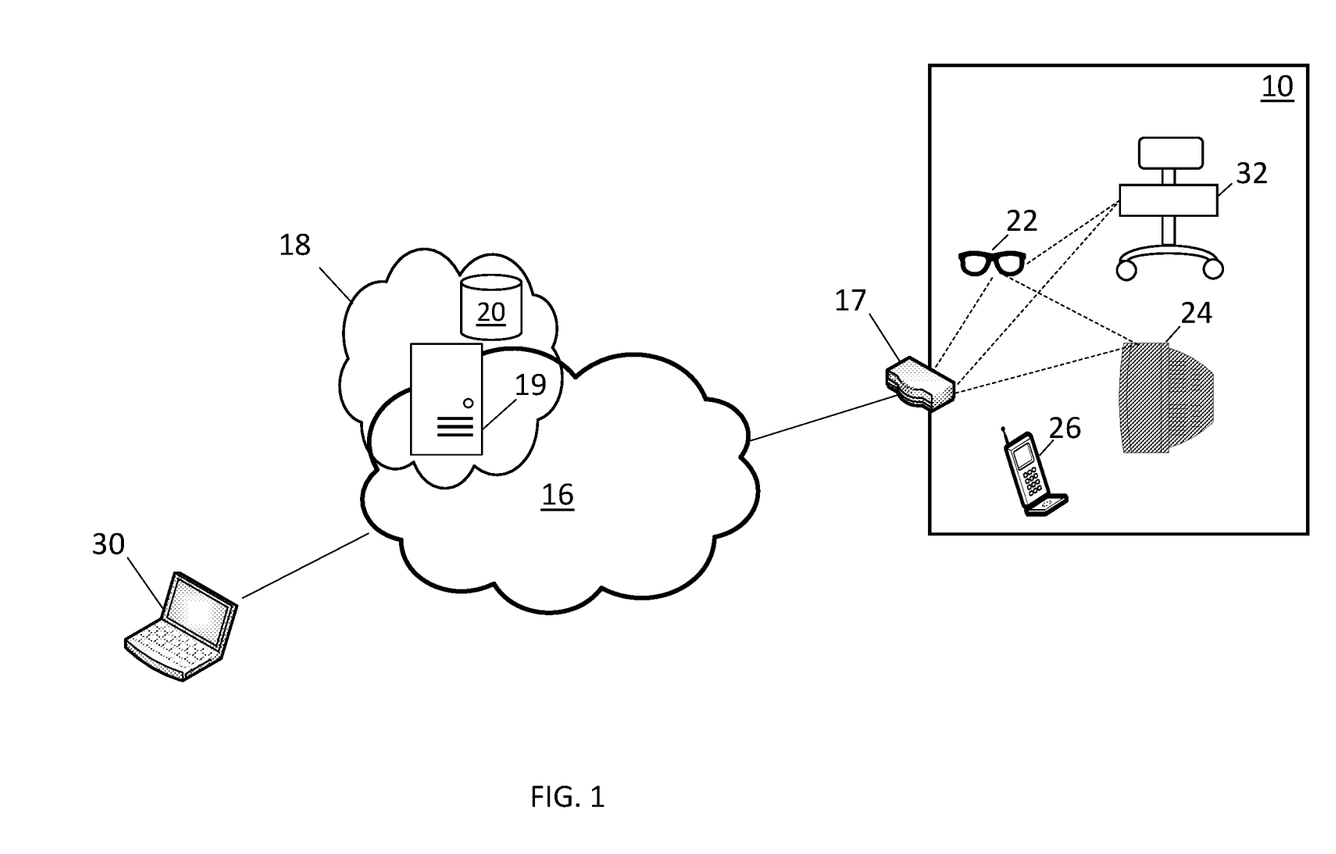
FIG. 1 is an illustrative network diagram of an environment in which embodiments of the present inventive concepts can be practiced.

FIG. 1 is an illustrative network diagram of an environment in which embodiments of the present inventive concepts can be practiced.

The environment illustrates a medical treatment room 10 or other healthcare facility such as an operating room, cloud computing environment 18 (referred to generally as a "cloud"), at least one computing device 30 of one or more remote users, and a cache or other data storage device of a cloud-based computer 19 each connected to a data communications network 16 to exchange data, video, audio, or a combination thereof with each other.

Examples of a communication network 16 may include, but are not limited to, a public switched telephone network (PSTN), wireless network such as a cellular network for mobile devices, a GPS network, a data communication network, or a combination thereof. In some embodiments, the medical treatment room 10 includes a set of electronic devices for communicating with the network 16, and in particular, with the cloud computing environment 18. This may include at least one network computer 17 such as a router or wiring closet electronic device having an I/O device such as a network interface that exchanges data with the network 16. In doing so, the network computer(s) 17 may be configured to form a mobile hotspot, WiFi network, or the like so that one or more remote computing devices 30 such as personal computers, smartphones, and the like can exchange data, video, audio, or a combination thereof as part of a communication session with stationary and/or mobile electronic devices in the medical treatment room 10. For example, positioned in the room 10 may include one or more mobile computing devices 22 such as a wearable device. e.g., a camera and processor integrated into a pair of goggles, or a virtual wearable computer such as Google Glass™, fixed or immobile electronic devices of an infrastructure such as an operating room, which can include infrastructure clients 24, e.g., a videoconferencing system 40 and/or portable devices or systems 32 such as a specialist camera mounted on boom arm trolleys(see FIG. 2). In some embodiments, the infrastructure client 24 communicates with the mobile computing device 22, for example, exchanges data, directly with no participation by the network 16. In some embodiments, a videoconferencing system 40 is the primary mechanism of the infrastructure client 24 for receiving and transmitting images, audio, and/or other multimedia information regarding a medical operation performed on a patient in the medical treatment room 10. In some embodiments, the videoconferencing system 40 is itself fixed, e.g., constructed to include a large bulky LCD screen, base, and relies on other portable cameras and/or microphones to collect video and/or audio feeds from other locations otherwise not accessible by the videoconferencing system 40. In other embodiments, the videoconferencing system 40 includes software executed on a smartphone or other small mobile device having a camera, microphone, and display screen. In some embodiments, the communication network 16 includes a cloud computing environment 18. In other embodiments, the cloud computing environment 18 is separate from and in electronic communication with the communication network 16.

Figure 2:
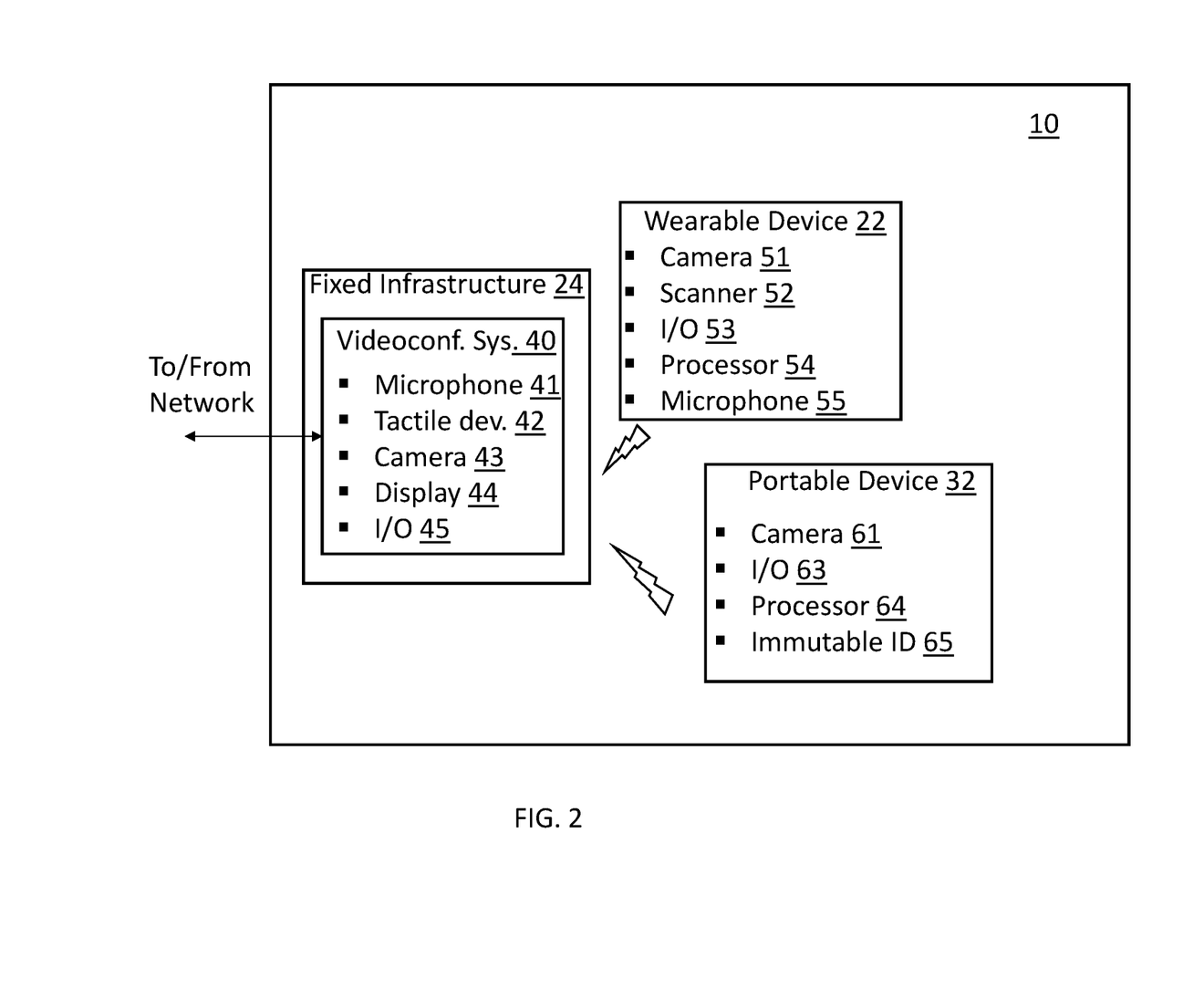
FIG. 2 is an illustrative diagram of a medical environment such as an operating room including a fixed surgical videoconferencing infrastructure and a mobile or wearable computing device seamlessly exchanging data, in accordance with some embodiments.

As shown in FIG. 2, the medical treatment room 10 can be any room in a healthcare facility for treating medical patients. The medical treatment room 10 may include well-known items such as a bed, table, sterilization items, and various medical equipment. The room may also include computer equipment such as network devices for communicating with the cloud computing environment 18 in the network 16, cloud-based computer 19, remote computing devices 30, and so on.

As described above, the medical treatment room 10 can include fixed or immobile electronic devices 24 such as a videoconferencing system, desktop computer, servers, and the like in an operating room. Some electronic devices 24 may be physically installed, for example, permanently coupled to a wall, floor, or other region of the room 10. Other electronic devices, while not permanently affixed in the room 10, may nevertheless be large, bulky, or otherwise impracticable or infeasible to move, and therefore deemed non-portable. Other electronic devices may be portable but not mobile such as specialist cameras mounted on boom arm trolleys.

Accordingly, embodiments of the fixed surgical videoconferencing system 40 includes a set of media input devices, such as cameras, microphones, tactile or haptic screen devices such as touchscreens or the like that can accept annotations over video and images, a computing device that distributes the media inputs to remote participants either peer-to-peer or via the cloud computing environment 18 depending on the infrastructure setup, and/or one or more display devices for the composite media feeds and any visual feedback from participants in a videoconferencing session, such as annotations, chat, and so on. The fixed infrastructure components may include Audio Video (AV) conferencing devices, loudspeaker(s), ancillary processors for audio and video, and one or more computer servers. In some embodiments, as shown in FIG. 2, a videoconferencing system 40 of the infrastructure client 24 may include a microphone 41, tactile electronic device 42 such as a tablet, keyboard, etc. for accepting annotations or the like over video and images, a camera 43, a display 44 such as a wall-mounted screen, and an input/output (I/O) device 45 such as a transceiver in communication with the network 16, e.g., Internet, cloud computing, private local area network, and so on. The I/O device 45 may also communicate with other electronic devices in the medical treatment room 10 such as a compatible I/O device 53 of the wearable device 22 and/or I/O device 63 of the portable device 32.

A mobile or wearable computing device 22 in the room 10, also referred to as a wearable device, includes wearable technology to seamlessly exchange data with the electronic devices of an infrastructure client 24. For example, the wearable device 22 can navigate to and start a videoconferencing session with the videoconferencing system 40 with minimal interaction. In another example, a wearable device can join a current videoconferencing session in progress by integrating with the videoconferencing system 40 at the point of use, i.e., in the medical treatment room 10.

In an example embodiment, the only requirement for initiating a videoconferencing session is to provide a line-of-sight path from the camera or other scanning device of the wearable computing device 22 and a QR code or the like displayed on a computer monitor that, when scanned, automatically triggers a data signal to be received by a processor of the videoconferencing unit, which in turn activates the session. This obviates the need for a surgeon or other user of the wearable device 22 to physically touch the videoconferencing system or the wearable device itself and preserve the sterility of the surgeon's hands. In other embodiments the surgeon may read aloud a unique sequence of digits to communicate to the wearable device by way of onboard speech recognition the information that would in the previous example embodiment be communicated by QR code. In some embodiments, when the camera enabled device is worn, its default state is for its camera to be active, and the wearable device is configured to act on a valid QR code that is in the field of view of the camera. In other embodiments when the wearable device is worn its default state is for the microphone to be active and speech recognition software to process human speech and commands. The wearable device 22 can perform both functions without compromising the sterile field of the medical treatment room 10, i.e., surfaces, instruments, and other objects in the room 10 as well as users of the wearable device 22 such as a surgeon, technician, or nurse with protective equipment, etc. In some embodiments, the wearable device 22 includes a camera 51 and/or scanning device 52 or related image sensing device that is capable of capturing video from the perspective of the user, i.e., surgeon or other practitioner. The camera 51 can stream the captured video processed by the processor 53 and output by an I/O device 54 such as a wireless transceiver to other participants such as users of the remote computing devices 30 by being integrated with the fixed infrastructure client 24. The videoconferencing system 40 can support multiple streams, so the additional video is sent to remote participants. Here, the same networking egress, e.g., same WiFi network, can be used. However, the wearable device 22 does not rely on any additional hardware to relay its signals to a computer facilitating a videoconferencing session. In some embodiments, the camera 51 can read a visual identifier such as a QR code or the like. In other embodiments, the microphone 55 can hear the voice of the operator and onboard software (stored in memory and executed by the processor 54), can interpret speech senses by the microphone 55. A visual or audio scanning device and/or software or processor can receive and process the visual or audio identifier information read by the camera 51 or microphone 55. In some embodiments, the camera or other scanning device of the wearable device 22 can read a visual identifier such as a machine-readable optical label, e.g., a QR code or the like displayed by a computer screen of the fixed infrastructure. In some embodiments, the wearable device 22 includes a mechanism to provide audio, visual, and/or haptic feedback to the wearer, for example, a speaker, vibrating mechanism, display, e.g., a virtual display on goggles of the wearable device 22, and so on. In some embodiments, the wearable device 22 includes augmented reality technology, which can capture and modify images of the medical treatment room 10 in real-time. For example, the wearable device 22 may add 3D images and information such as animations and videos, to the actual images captured by the videoconferencing system 40 and overlay the computer-generated or digital information on the actual images, and output the modified video, audio, and/or other data images, feeds, or the like for storage at the cloud-based computer 19 or use by a remote user 30.

The wearable device 22 and the fixed surgical videoconferencing system 40 are integrated in a manner to provide an electronic communication therebetween. To establish a communication, session details may be provided from the videoconferencing system 40 to the wearable device 22 by encapsulating a reference to the session that can only be processed, e.g., decoded or interpreted, by the wearable device 22. In some embodiments, the session details may be provided by the portable device 32 if the portable device 32 has a user logged into a session. The session state details may be copied and provided to the wearable device 22 such that the wearable device 22 can instantly access the same information accessed by the videoconferencing system 40 in a secure manner. In order to perform such a "copy," embodiments of the present inventive concept include a computer-implemented process that protects the information while allowing authorized users to make use of it.

The portable device 32 and the fixed surgical videoconferencing system 40 are likewise integrated in a manner to provide an electronic communication therebetween, and so that the portable device 32 can be seamlessly integrated a videoconferencing session performed by the videoconferencing system 40, or where the camera 61 of the portable device 32 can serve as a camera for the fixed infrastructure client 24, which may have a processor, I/O, and so on for exchanging data streams with the remote computer 30 but relies on the camera 61 of the portable device 32 to provide camera images, video, and the like for exchange with the remote computer 30. In some embodiments, the fixed infrastructure client 24 includes a router or the like to provide network access via its I/O device 45. The portable device 32 may connect directly to the cloud server 19 via a 4G/5G network connection or the like irrespective of whether the fixed infrastructure client 24 manages the connection. Accordingly, a session may be performed entirely on a smartphone or other mobile device without the fixed infrastructure client 24. In other embodiments, other peripheral devices such as microphones, sensors, keyboards, and so on may be integrated from the portable device 32 into an electronic communication between the fixed infrastructure client 24 and remote computer 30.

Figure 3:
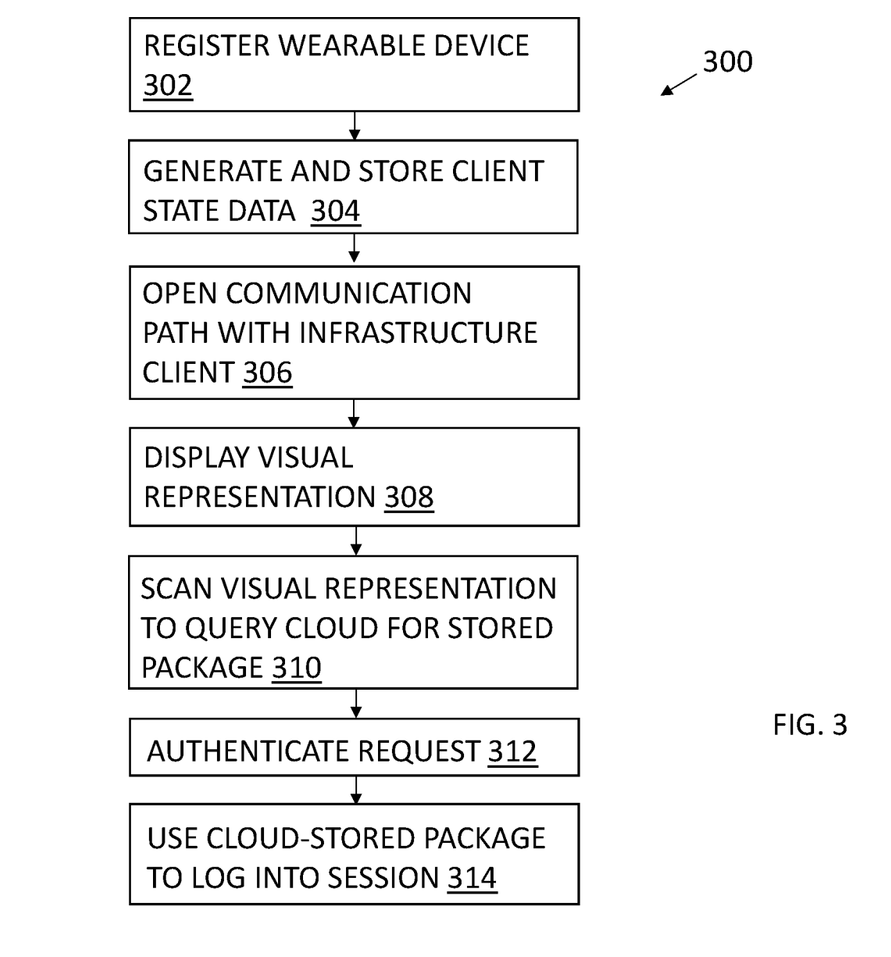
FIG. 3 is a flow diagram of a method of executing a session data transfer between a mobile or wearable computing device and a stationary computing device, in accordance with some embodiments.

FIG. 3 is a flow diagram of a method 300 of executing a session data transfer between a mobile or wearable computing device and a stationary computing device, in accordance with some embodiments. In describing the method 300, reference may be made to elements of FIGS. 1 and 2. For example, as shown in FIG. 2, the method 300 can be performed by at least the wearable device 22 and the fixed infrastructure client 24 in the medical treatment room 10.

At block 302, a wearable computing device 22 may register with a cloud-based computer 19 for security purposes, for example, as part of a cloud-based authentication. The registration type may depend on the required security policy. For example, a single user of the wearable computing device 22 may be registered, or a group of users associated with an entity such as a hospital, business, or other commercial enterprise. In some embodiments, the registration includes the creation of a cryptographic key pair (public/private; encryption/decryption, etc.) between the wearable device 22 and a cloud-based computer server (also referred to as a cloud-based computer) 19 of the cloud computing environment 18 so that the wearable computing device 22 can be authenticated as a registered device. In creating a key pair, certificate pair, or the like, the wearable computing device 22 may sign subsequent requests due to a unique index assigned to a stored package (described below) that allows that package to be retrieved again. With regard to signing subsequent requests, the wearable computing device 22 can generate a private key/public certificate pair at the point of registration. As is well-known in the field of cryptography, data that is encrypted with the private key can only be decrypted by the certificate. Accordingly, the wearable device 22 proves its identity by encrypting a hash of any message with its key. Since only the corresponding certificate can decrypt it, the message is provably from the wearable device. This allows many derivatives of the method 300 to be performed, whereby a wearable computing device 22 that is associated to a user group can be refused entry/automatically admitted to a session because it is provably a known device.

At block 304, a fixed infrastructure client such as the videoconferencing system 40 generates session state information, which can be encapsulated in a data unit, such as a packet or frame, referred to as a package. The videoconferencing system 40 must be in a video and/or audio communication exchange with the remote device 30 at the time that the session state information is generated. Client-side session state information may include information about a current state of the infrastructure client 24, which may include but not be limited to a login status, user display preferences, and/or other data elements associated with the session state, for example, information that is preferable to a user with respect to a presentation of video, audio, and/or multimedia on a computer display for the user. The current state information output from the fixed infrastructure client computing device 40 to a server-side process, for example, can be stored at the cloud computing environment 18. This may include a key value regarding the cryptographic key pair described in block 302. In other embodiments, the client computing device 40 may generate a universally unique identifier (UUID) or related index. Other local client state information that may be encoded may include, but not be limited to information related to preferred ordering or focus of feeds display (described below), preferred white balance, information whether other real time data such as heart rate or blood pressure is shown on the feed, and/or muted or unmuted microphone or speakers.

At block 306, the server 18 in communication with the cloud-based computer 19 can open a computer communications connection, for example, a Web Socket connection, for establishing a two-way electronic communication with the client 24 for exchanging the packets, frames, or other data units formed in block 304. The cloud-based computer 19 can exchange data via the network 16. Alternatively, configurations may be present where the computer server 18 is not part of a cloud computing environment but is nevertheless configured to generate a Web Socket or the like, example, via a wireless connection via the network computer 17 or via a direct connection.

At block 308, a visual representation of the key value of the stored state is generated and displayed on the display 44 of the videoconferencing system 40. In some embodiments, the visual representation can be displayed on a separate display of the tactile device 42. In some embodiments, the visual representation is in the form of a QR code or the like.

At block 310, the camera of the wearable device 22 can capture an image of the QR code or other visual representation. The contents of the image can be processed by the QR code processing software of the wearable device 22 or stored at a remote computer. The QR code can be used to query the cloud computing environment 18 for the store package, i.e., stored by the fixed infrastructure client 24, e.g., videoconferencing system 40, in block 304.

At block 312, the cloud-based server authenticates the user's request at block 304 and validates the client request at block 304 to store the package including session details. Having answered the session state, the cloud-based computer 19 can communicate to the fixed infrastructure client computing device 40 that the session package has been used. In some embodiments, according to a predetermined security policy, the fixed infrastructure client computing device 40 may generate a new session package for additional wearable devices, or to remove the QR code from the client display 44.

At block 314, the wearable device 22 can use the cloud-stored package to log into the session. In particular, stored package may contain at least a session token or other security-related data that is transferable to another device, such as another cloud server, which may relate on the token or other issued data artifact for use by a computer-based apparatus, for example, having a camera for participating in a videoconferencing session and allows an instant login to the session.

Figure 4:
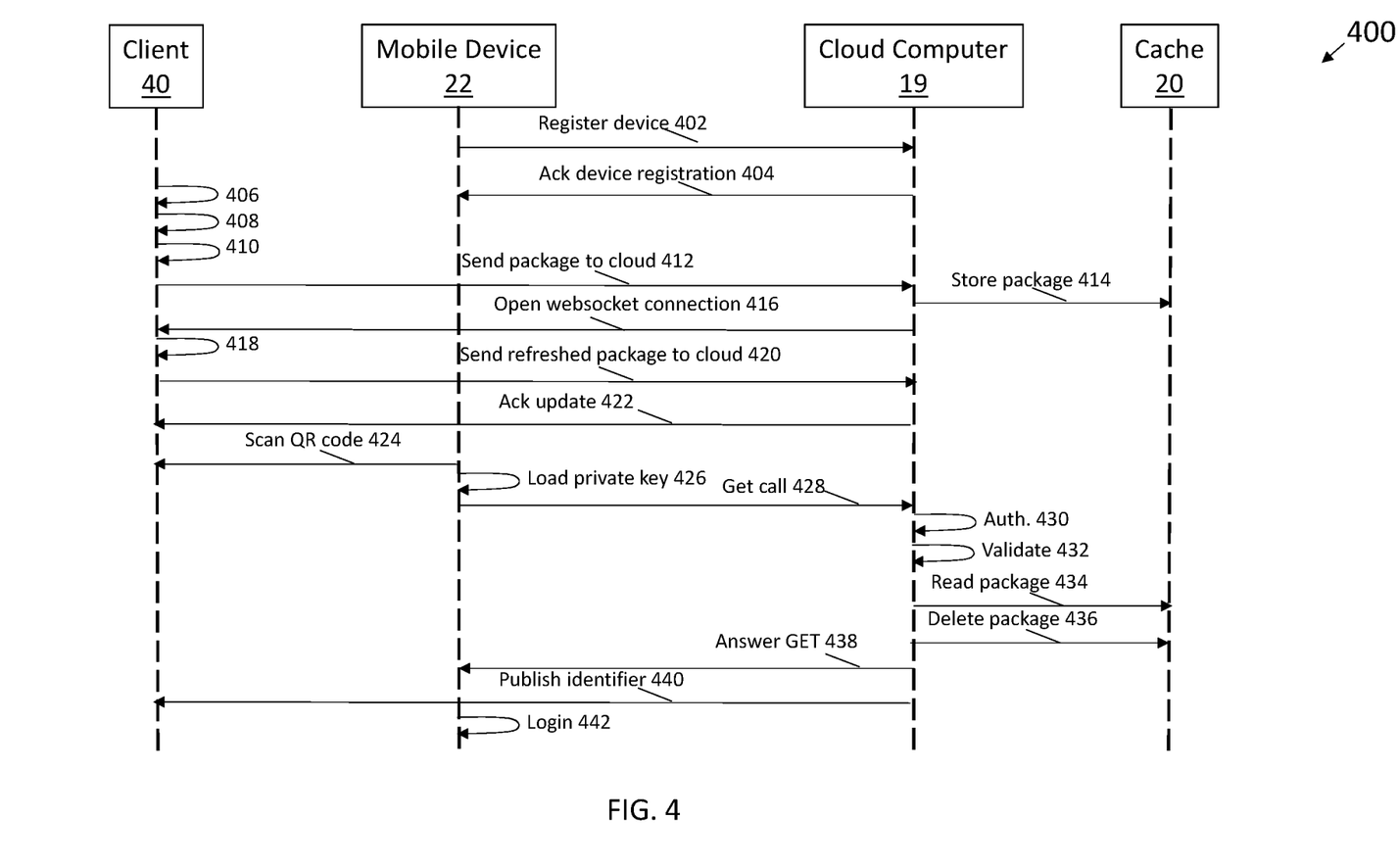
FIG. 4 is a block diagram of a system for facilitating a session data exchange between a mobile or wearable computing device and a stationary computing device, including data flow paths between elements of the system, in accordance with some embodiments.

FIG. 4 is a block diagram of a system 400 for facilitating a session data exchange between a mobile or wearable computing device and a stationary computing device, including data flow paths between elements of the system 400, in accordance with some embodiments. The system 400 can include the videoconferencing system 40 of the infrastructure client 24, the wearable device 22, the cloud-based computer 19, and storage device of the cloud-based computer 19 of FIGS. 1 and 2, so details thereof are not repeated for brevity. At least some of the data flow paths may be part of the method 300 described with respect to FIG. 3.

Prior to the session data exchange, the wearable device 22 is registered with the cloud-based server 18, for example, described with respect to block 302 of the method 300 of FIG. 2. In some embodiments, the registration process includes the creation of a cryptographic key or certificate pair, e.g., generating public and private keys according to well-known encryption techniques, permitting the wearable device 22 to sign subsequent requests and be authenticated as the registered device. Accordingly, the wearable device 22 can be registered by generating and outputting, at flow path 402, a digital certificate, e.g., including an encrypted key or the like, to the cloud-based computer 19. The digital certificate can be processed by the cloud-based computer 19, which in response at flow path 404, can acknowledge the registration of the wearable device 22. Accordingly, the certificate can authenticate the identity of the wearable device 22 in a public key infrastructure or the like.

At flow path 406, the fixed infrastructure client 24, e.g., the videoconferencing system 40, may obtain a session identifier from the cloud-based computer 19. The client 24 may generate a UUID which may be processed as part of a key-based authentication or other security process. As described below, the UUID may be visually displayed on a computer display of the fixed infrastructure client 24 as a QR code or the like, which can be scanned by the wearable device 22 to retrieve session information corresponding to the UUID. As with the other flow paths, flow path 406 may occur before, after, or concurrently with flow path 404. In some embodiments, the session identifier as used in one or more flow paths of the session data exchange complies with a communication protocol such as SIP. The fixed infrastructure client 24 can query itself after the session has been created and the communication protocol, e.g., SIP, has created a session identifier on which both the client 24 and cloud-based computer 19 agree.

At flow path 408, the fixed infrastructure client 24 can obtain additional session information, for example, information created on the client with respect to the session (not additional session attributes). For example, information may include an arrangement of video feeds on a computer display of the wearable device 22, and whether the microphone 55 should be muted or active.

At flow path 410, a package or the like can be generated by the fixed infrastructure client 24 that includes a session token or other security-based token and the obtained session information. The package may be encapsulated in a data unit such as a frame or packet or other data unit for electronic exchange in the flow paths of the data exchange shown in FIG. 4. The session identifier and additional session information of flow paths 406 and 408 may be part of the package.

At flow path 412, the package including the encapsulated state data is output from the client 24 to the cloud computing environment 18, where it can be temporarily stored. In some embodiments, at flow path 414, the current state data can be transferred to the storage device of the cloud-based computer 19, where a key value is generated, i.e., by the cloud-based computer 19, that includes a unique index that allows the package to be identified and retrieved from a cache or the like of the storage device of the cloud-based computer 19. In some embodiments, the stored package is first keyed by the UUID generated by the infrastructure client 24, e.g., videoconferencing system 40.

At flow path 416, the cloud-based computer 19 responds to the UUID and opens a WebSocket connection or the like with the infrastructure client 24. At flow path 418, the client computing device 40 displays the UUID as a QR code or other visual indicator. At flow path 420, the client computing device 40 may send a refreshed or updated package using the UUID to the cloud 18 in response to a user-initiated change from the client. For example, the client-side state may change, for example, a display preference such as an ordering of feeds. For example, the videoconferencing system 40 in a current session with remote videoconferencing systems may change the order in which the remote systems are displayed. In another example, the client-side state may change by muting or unmuting a microphone or speaker, changing a white balance setting, etc. The WebSocket connection is used to provide the changed client information to the cloud-based computer 19, which at flow path 422 outputs an acknowledgement update to the client computing device 40.

At flow path 424, the wearable device 22, or more specifically, the camera 51 and/or other scanning device 52 or sensor, scans the machine-readable code, e.g., QR code or other visual identifier, at the infrastructure client 24, for example, displayed at the videoconferencing system 40. The data acquired from the scanned code can be used to query the cloud computing environment 18 for the stored package containing the necessary session credentials to permit the wearable device 22 to join a data communication exchange of interest, i.e., a videoconference between the videoconferencing system 40 and remote computing devices 30. At flow path 426, the wearable device 22 loads a private key or other encryption feature generated during registration at block 402. This step allows the wearable device to prove its identity and registration. It may, for example, deny entry to a legitimate user of the teleconferencing platform from using a stolen or incorrectly licensed device. Therefore, although a device may be allowed into a session, the user of the device may not be allowed into the session.

At flow path 428, the wearable device 22 may generate and output a request to the cloud 18 for validation. In some embodiments, this may include a signed GET call to a URL for a UUID keyed resource. At flow path 430, the cloud-based computer 19 authenticates the client signature by matching the client signature with the registered wearable device 22, and at flow diagram 432 validates that the authenticated user may access the stored package.

At flow path 434, the cloud-based computer 19 reads the package keyed by UUID, and at flow path 436 deletes the stored package keyed by the UUID. At flow path 438, the cloud-based computer 19 answers the GET call 428 with the UUID keyed package. At flow path 440, the cloud-based computer 19 publishes the identified accessible to the client computing device 40. At flow path 442, the wearable device 22 uses the session token, session ID, or other credential information of the package required to join a communication session with the videoconferencing system 40 and remote participant(s) 30. The credential information may be transferable. For example, a session token of the package may use the token or other cloud server issued data artifact that allows an instant login function to be performed another computing device interested in participating in the communication session.

Figure 5:
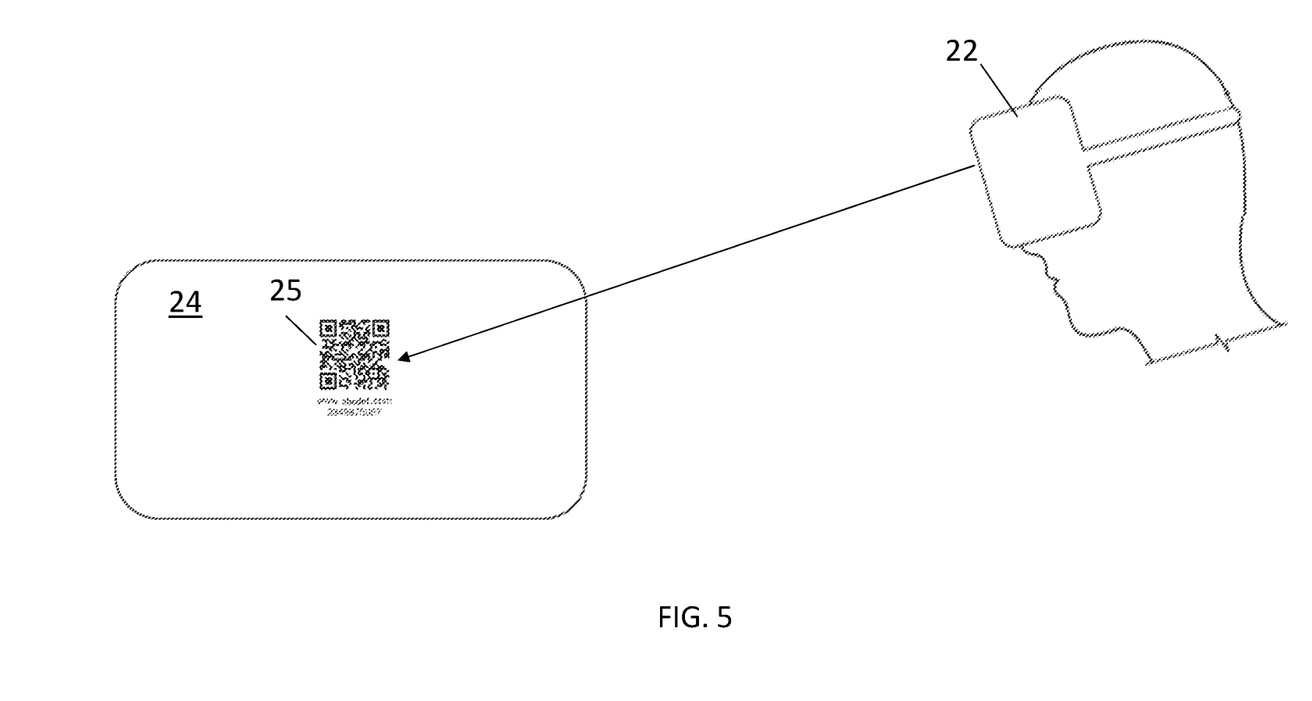
FIG. 5 is an illustrative diagram of an operation performed by the system of FIGS. 1-4, in accordance with some embodiments.

As shown in FIG. 5, a client infrastructure 24 may display a machine-readable code 25 such as a QR code or the like generated by a computer processor of the infrastructure client 24 in response to a command issued by an operator of the wearer device 23, or at the time of required use. The machine-readable code 25 includes location information such as a key value or UUID that allows the session information stored at the cloud cache 20 to be retrieved so that the wearable device 22 can join a communication session, e.g., a videoconference, with the videoconferencing system 40 of the client infrastructure 24. The wearer device operator command may be made by a verbal utterance that is received by a microphone 55 or the like. In other cases, a command can be provided by a foot pedal in communication with the infrastructure 24 via Bluetooth™ or other wired or wireless connection. The Bluetooth™-enabled foot pedals can be preprogrammed to participate in particular operations. This feature illustrated in FIG. 5 may further limit the ability of an unauthorized person to compromise the session because a registered device is required, and in addition, a line of sight between the wearable device 22 and the QR code 25 is required at the exact moment that the QR code 25 is displayed.

Another feature is that the machine-readable code can be presented to multiple remote computing devices 30 at the instruction of the wearer device operator, which allows for similarly registered devices to provide temporary video feeds from their own locations. For example, during a medical procedure when a tumor is removed, tissue samples are taken from around where the tumor was and sent to a pathology lab for analysis in real time to ensure that the entire tumor was removed. Here, a pathology laboratory specialist can share the feed from the microscope directly with the surgeon via a videoconferencing session and discuss the findings or in lower tech settings, for example, sharing the feed by the specialist wearing the wearable device 22, looking at the watch or the like, and then looking at the screen or directly into the microscope, the display being received by the wearable device and shared via video with the surgeon. This feature is not restricted to wearable devices but can permit a remote user at a personal computer to generate push notification of the QR code to a wearable device such as a smart watch and immediately start a feed into the session.

Figure 6:
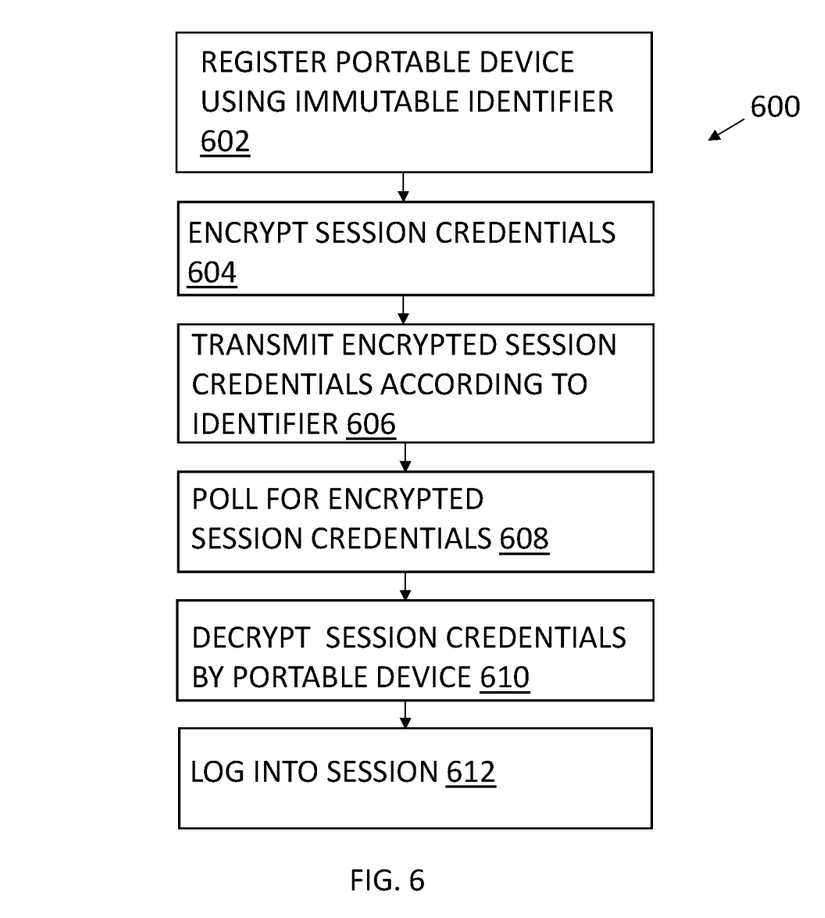
FIG. 6 is a flow diagram of a method of executing a session data transfer between a mobile or wearable computing device and a stationary computing device, in accordance with some embodiments.

FIG. 6 is a flow diagram of a method 600 of executing a session data transfer between a mobile or wearable computing device and a stationary computing device, in accordance with some embodiments. In describing the method 600, reference may be made to elements of FIGS. 1 and 2. For example, referring to FIG. 2, the method 600 can be performed by at least a wearable device 22, a smartphone or other mobile device 26, a portable device 32 such as a camera on a trolley, and a fixed infrastructure client 24 in the medical treatment room 10. In some embodiments, a same or similar asymmetric cryptography process is performed as part of a method of FIG. 3 or 4.

At block 602, for entry into the session, the smartphone 26 may register with a cloud-based computer 19. The portable device 32 has an immutable identifier 65 such as an RFID or NFC tag or machine-readable code such as a QR code that includes information about the portable device 32 for registration, for example, a number of onboard cameras, a confirmation of audio capabilities, and so on, which can be used for generating a cryptographic key/certificate pair or the like. The mobile device 26 can be invited into a session by executing a mobile application to read the RFID or NFC tag or QR code to authenticate the device to which the tag is attached for use in the session. In some embodiments, the registration includes the creation of a digital certificate, public cryptographic certificate, or the like associated with the immutable identifier 65, which is transmitted from the portable device 32 to a cloud storage device 20, e.g., a cache, of the cloud computing environment 18 for storage.

At block 604, a fixed infrastructure client 24 generates and encrypts session credential information required for joining a communication session such as a video communication exchange between the videoconferencing system 40 and remote computer 30. In some embodiments, the session credential information can include state information, for example, similar to information described in steps 406, 408, and 410 in FIG. 4. In some embodiments, the fixed infrastructure client also acquires the information from the immutable identifier 65, for example, by a mobile device scanning the RFID or NFC tag on the portable device 32. In some embodiments, the session credentials are encrypted using a public cryptographic certificate of the fixed infrastructure client 24.

At block 606, the session credentials encrypted using the public certificate are transmitted from the fixed infrastructure client 24 to the cloud computing environment 18. In some embodiments, the encrypted session credentials are stored at a cloud storage device 20 of the cloud-based computer 19, e.g., a cache, according to instructions associated with the immutable identifier 65.

At block 608, the portable device 32 performs a polling operation for a constant URL, for example, transmitting an HTTP GET Call request or the like to the server of the cloud computing environment 18. In response, the cloud server transmits the stored encrypted session credentials originating at the fixed infrastructure client 24 to the portable device 32. At block 610, the portable device decrypts the session credentials using the associated public certification stored at the cloud storage device 20.

At block 612, the portable device 32 can use the decrypted session credentials to log into the session. In particular, stored package may contain at least a session token or other security-related data provided by the client 24. This information can be transferable to another device, such as the wearable device 22, which may relate on the token or other issued data artifact for use by a computer-based apparatus, for example, having a camera for participating in a videoconferencing session and allows an instant login to the session.

Accordingly, in the method 600, an asymmetric cryptography process is performed. Namely, the session credentials encrypted by public certificate can only be decrypted by the associated private key and the information signed or encrypted by the private key, e.g., outbound information, can only be decrypted by the associated public certificate. Cryptographic techniques including encrypting by public certificate and decrypting by key provides for protection against interception, while encrypting by private key/decrypting by certificate provides for protection against spoofing. Since the wearable device 22 can retain a private key and publish an associated public certificate, the contents encrypted by the private key are only decrypted by the associated certificate originating from the wearable device 22. In this manner, users can be denied access who are not permitted to use the device 22 in a particular session.

Figure 7:
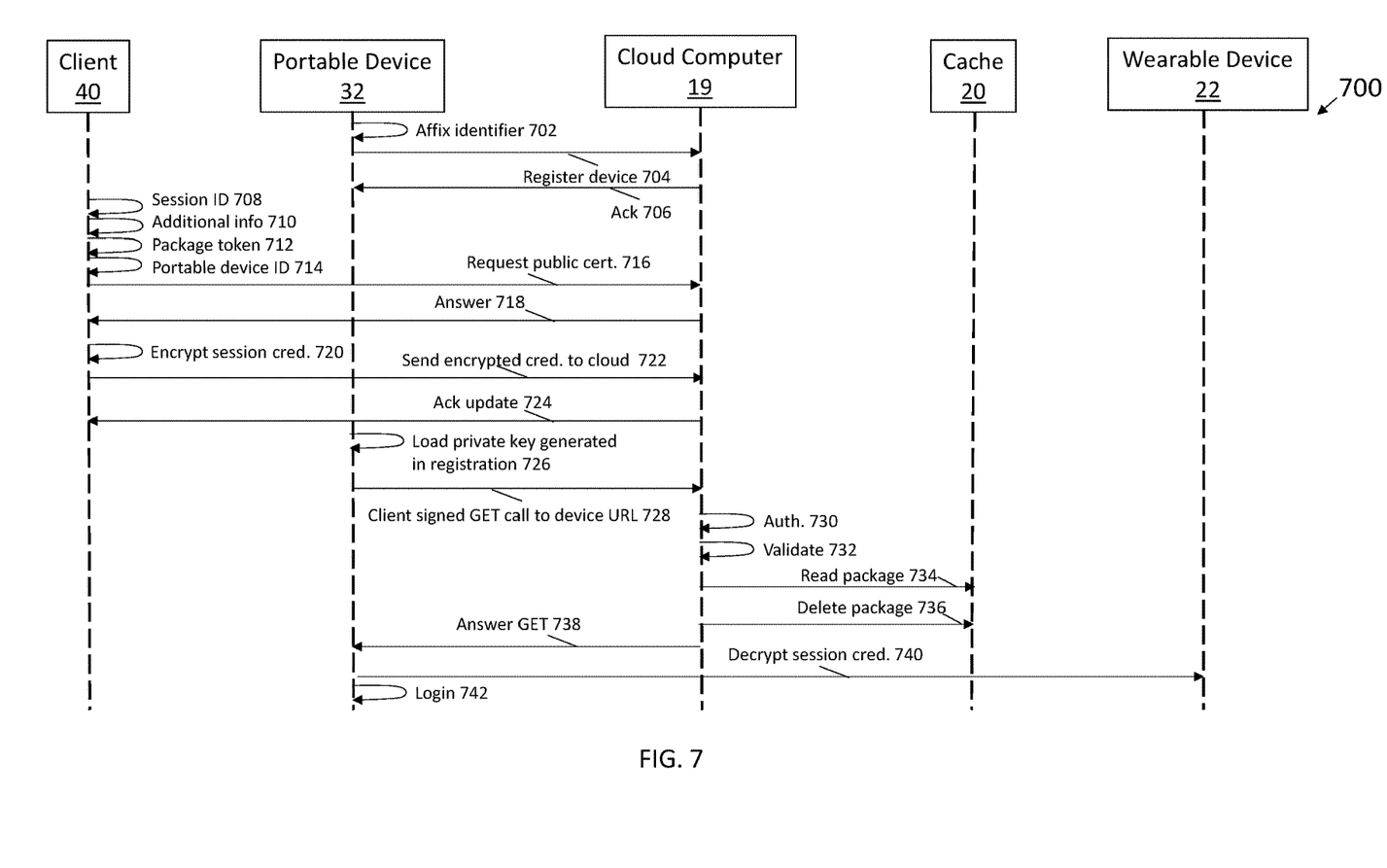
FIG. 7 is a block diagram of a system for facilitating a session data exchange between a mobile or wearable computing device and a stationary computing device, including data flow paths between elements of the system, in accordance with some embodiments.

FIG. 7 is a block diagram of a system 700 for facilitating a session data exchange between a mobile or wearable computing device and a stationary computing device, including data flow paths between elements of the system 700, in accordance with some embodiments. The system 700 can include the videoconferencing system 40 of the infrastructure client 24, the portable device 32 such as specialist camera mounted on a boom arm trolley, the cloud-based computer 19, and storage device 20 of the cloud-based computer 19 of FIGS. 1 and 2, for example, a cache, so details thereof are not repeated for brevity. At least some of the data flow paths may be part of the method 300 described with respect to FIG. 3.

At flow path 702, an immutable identifier 65 is affixed to the portable device 32. The immutable identifier 65 can be an RFID or NFC tag or machine-readable label, for example, a QR code. In some embodiments, the identifier is a physical object affixed to the portable device 32. In other embodiments, the identifier 65 is generated electronically and displayed at an LCD or other electronic display of the portable device 32, or a computer such as a laptop or smartphone in electronic communication with a processor of the portable device 32.

At flow path 704, the portable device 32, or a computer such as a laptop or smartphone operating as a proxy for the portable device 32, is registered with the cloud-based computer 19. The registration may include the creation of a cryptographic key/certificate pair. In doing so, the portable device 32 or proxy device can generate and output a digital certificate associated with the immutable identifier 65 to the cloud-based computer 19. For example, the generation process at the point of registration can use the immutable identifier as a portion of the certificate. In some embodiments, the certificate is a public certificate used for encrypting session credentials (described below). The cryptographic key may be a private key used to decrypt the encrypted session credentials. In response to receipt of the certificate by the cloud-based computer 19, the cloud-based computer 19 at flow path 706 can acknowledge the registration of the wearable device 22.

At flow path 708, the fixed infrastructure client 24, or more specifically, the videoconferencing system 40, may obtain a session identifier. For example, the client 24 may generate a QUID which may be used by the cloud-based computer 19 as part of a key-based authentication or other security process. As with the other flow paths, flow path 708 may occur before, after, or concurrently with another flow path such as flow path 706. In some embodiments, the session identifier complies with a communication protocol such as SIP. The client 24 can query itself after the session has been created and the communication protocol has created a session identifier on which both the client 24 and cloud-based computer 19 agree.

At flow path 710, the fixed infrastructure client 24 can obtain additional session information, for example, information created on the client with respect to the session (not additional session attributes). For example, such information may include an arrangement of video feeds on the wearable screen, and whether the microphone 41 should be muted or active.

At flow path 712, a package or the like can be generated by the client 24 that includes a session token or other security-based token and the obtained session information. The package may be encapsulated in a data unit such as a frame or packet. The session identifier and additional session information of flow paths 708 and 710 may be part of the package.

At flow path 714, the client 24 obtains the immutable identifier 65 of the portable device 32. In some embodiments, the immutable identifier 65 is part of the package. For example, the client 24 can obtain the immutable identifier 65 by waving the user smartphone 26 at the NFC tag with that smartphone 24 logged into the session. The information obtained in flow paths 708-714 may collectively be referred to as session credentials to be encrypted.

At flow path 716, the client sends a request for the cryptographic certificate of the portable device 32 from the cloud-based computer 19 for encrypting the session credentials, e.g., session token, session ID, and so on. At flow path 718, the cloud-based computer 19 replies to the request. At flow path 720, the client encrypts the session credentials using the public cryptographic certificate. At flow path 722, the client sends the encrypted session credentials to the cloud-based computer 19. For example, the client-side state may change, for example, a display preference initiated from the client computing device 40 such as an ordering of feeds. At flow path 724, the cloud-based computer 19 outputs an acknowledgement update to the client computing device 40.

At flow path 726, the portable device 32 may load a private key or other encryption feature generated at flow path 704, which can be used for decrypting the session credentials encrypted by the public cryptographic certificate. As shown below, the private key can be exchanged between the portable device 32 and the wearable device 22 so that the wearable device 22 can decrypt the session credentials encrypted in flow path 720. At flow path 728, the portable device 32 may send a request to the cloud 18 for validation. In some embodiments, this may include a signed GET call to a URL for a UUID keyed resource. The URL is associated with the device of interest. At flow path 730, the cloud-based computer 19 authenticates the client signature by matching the client signature with the registered portable device 32, and at flow diagram 732 validates that the authenticated user may access the stored package.

At flow path 734, the cloud-based computer 19 reads the package keyed by UUID, and at flow path 736 deletes the stored package keyed by the UUID. At flow path 738, the cloud 18 answers the GET call with the UUID keyed package. At flow path 740, the wearable device 22 can be a participant in a communication session with the portable device 32, client 24, and remote computing device(s) 30. In response to the encrypted session credentials sent from the cloud-based computer 19 to the portable device in flow path 738, the portable device 32 can decrypt the encrypted session credentials using the private key loaded at flow path 726 and associated with the portable device public certificate. The decrypted session credentials at flow path 740 can be sent to the wearable device 22. At flow path 742, the device uses the session token, session ID, or other credential information to log into the session with the videoconferencing system 40 and remote participant(s) 30. The credential information may be transferable, for example, exchanged by another cloud server issued data artifact that allows an instant login function to be performed by the wearable device 22.

As will be appreciated by one skilled in the art, aspects of the present invention may be embodied as a system, method, and apparatus. Thus, some aspects of the present invention may be embodied entirely in hardware, entirely in software (including, but not limited to, firmware, program code, resident software, microcode), or in a combination of hardware and software.

While various examples have been shown and described, the description is intended to be exemplary, rather than limiting and it should be understood by those of ordinary skill in the art that various changes in form and detail may be made therein without departing from the scope of the invention as recited in the accompanying claims.

What is claimed is:

1. A method for performing a secure data transfer between computing devices, comprising:

registering a resource-constrained computing device with a cloud-based computer;

generating, by a client computing device, session state information regarding the client computing device in an electronic communication exchange with at least one remote computing device;

storing the session state information at the cloud-based computer;

generating an identifier that provides a location of the session state information stored at the cloud-based computer;

displaying a machine-readable code associated with the identifier for querying the cloud-based computer for the stored session state information;

processing, by the resource-constrained computing device, the machine-readable code to retrieve the session state information from the cloud-based computer; and processing, by the resource-constrained computing device, the session state information to integrate the resource-constrained computing device with the client computing device to participate in the electronic communication exchange with the at least one remote computing device, the method further comprising:

determining a client-side change in the session state information;

sending a refresh state of the session state information including the client-side change to the cloud-based computer;

storing at the cloud-based computer the refresh state of the session state information;

providing the stored refresh state of the session state information a key value including a unique index generated by the cloud-based computer in response to a request by the stationary computing device to store the stored refresh state of the session state information; and displaying the machine-readable code as a visual representation of the key value.

2. The method of claim 1, wherein the resource-constrained computing device includes a wearable computing device.

3. The method of claim 1, wherein the session state information includes a token that permits the resource-constrained computing device to participate in the electronic communication exchange.

4. The method of claim 1, wherein registering the resource-constrained computing device includes generating an asymmetric key encryption scheme for securing the session state information.

5. The method of claim 1, wherein registering the resource-constrained computing device includes creating a cryptographic key/certificate pair so that the resource-constrained computing device can sign subsequent requests and be authenticated as a registered device.

6. The method of claim 1, wherein the data communication exchange complies with a Session Initiation Protocol (SIP).

7. The method of claim 1, further comprising:
generating, by the stationary computing device, a unique index; and
retrieving, by the wearable device, the session state information according to the unique index.

8. The method of claim 1, wherein the electronic communication exchange includes an exchange of at least one of video, audio, and data.

9. A method for performing a secure data transfer between computing devices, comprising:
- registering a portable device with a cloud-based computer, including:
  - generating a public cryptographic certificate associated with an immutable identifier of the portable device; and
  - generating a private key associated with the public cryptographic certificate;
- generating, by a client computing device, session credentials regarding an electronic communication exchange between the client computing device and at least one remote computing device;
- encrypting the session credentials using the public cryptographic certificate;
- storing the encrypted session credentials at the cloud-based computer;
- decrypting, by the portable device, the encrypted session credentials using the private key; and
- processing, by the portable device, the session credentials to integrate the portable device with the stationary computing device to participate in the electronic communication exchange with the client computing device and at least one remote computing device, the method further comprising:
- determining a client-side change in the session credentials;
- sending a refresh state of the session credentials including the client-side change to the cloud-based computer;
- storing at the cloud-based computer the refresh state of the session credentials;
- providing the stored refresh state of the session credentials a key value including a unique index generated by the cloud-based computer in response to a request by the stationary computing device to store the stored refresh state of the session credentials; and
- displaying a machine-readable code as a visual representation of the key value.

10. The method of claim 9, further comprising: using a mobile computing device logged into a session including the electronic communication exchange to obtain the immutable identifier.

11. The method of claim 9, wherein the session credentials include the immutable identifier.

* * * * *